United States Patent [19]

Allard et al.

[11] Patent Number: 5,616,331
[45] Date of Patent: Apr. 1, 1997

[54] STORAGE-STABLE, ULTRAFINE OIL-IN-WATER EMULSION NANOPIGMENTED SUNSCREEN/COSMETIC COMPOSITIONS

[75] Inventors: Delphine Allard, Colombes; Jean-Marc Ascione; Isabelle Hansenne, both of Paris, all of France

[73] Assignee: L'Oreal, Paris, France

[21] Appl. No.: 386,092

[22] Filed: Feb. 9, 1995

[30] Foreign Application Priority Data

Feb. 9, 1994 [FR] France .................. 94 01455

[51] Int. Cl.⁶ .................. A61K 7/06; A61K 7/44; A61K 7/48
[52] U.S. Cl. .................. 424/401; 424/70.1; 424/59; 424/60; 424/405
[58] Field of Search .................. 424/401, 405, 424/70.1, 60, 59

[56] References Cited

FOREIGN PATENT DOCUMENTS 0518773 12/1992 European Pat. Off. .
0559319 9/1993 European Pat. Off. .
9210995 7/1992 WIPO .

OTHER PUBLICATIONS

Serge et al., Chemical Abstracts, vol. 118, 1992, #131,766.
Martine et al., Chemical Abstracts, vol. 118, 1992, #175, 515.

Primary Examiner—Thurman K. Page
Assistant Examiner—D. Faulkner
Attorney, Agent, or Firm—Burns, Doane, Swecker & Mathis, L.L.P.

[57] ABSTRACT

Stable and homogeneous, topically applicable sunscreen/cosmetic compositions well suited for the photoprotection of human skin and/or hair against the damaging effects of UV-A and/or UV-B irradiation, particularly solar radiation, and which display excellent transparency on the skin, comprise a storage-stable, ultrafine oil-in-water emulsion of a photoprotecting effective amount of homogeneously and finely dispersed particulates of at least one inorganic nanopigment which comprises a metal oxide, for example titanium dioxide, wherein the average particle size of the globules comprising the oily phase of the emulsion characteristically range from 100 nm to 1,000 nm.

34 Claims, No Drawings

STORAGE-STABLE, ULTRAFINE OIL-IN-WATER EMULSION NANOPIGMENTED SUNSCREEN/COSMETIC COMPOSITIONS

BACKGROUND OF THE INVENTION

1. Field of the Invention

The present invention relates to novel cosmetic compositions for topical application, for the photoprotection of the skin and/or hair against ultraviolet radiation (such compositions hereinafter simply designated "sunscreen" or "sunscreen/cosmetic" compositions), to a process for the formulation thereof and also to the use of same for the cosmetic applications indicated above.

This invention more especially relates to the aforesaid sunscreen/cosmetic compositions, having improved properties and comprising oil-in-water type emulsions (in a cosmetically acceptable vehicle or carrier) that contain, as photoprotective agents which physically block the radiation (UV reflecting and/or diffusing agents), inorganic nanopigments based on the metal oxides, especially titanium dioxide.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B, causes erythema and burning of the skin which can impair the development of a natural tan; hence, such UV-B radiation must be screened from the skin.

It is also known to this art that UV-A radiation, of wavelengths from 320 to 400 nm, which tans the skin, also adversely affects it, in particular in the event of a sensitive skin or a skin continually exposed to solar radiation.

UV-A rays cause in particular, a loss in the elasticity of the skin and the appearance of wrinkles leading to a premature aging thereof. Such irradiation promotes triggering of the erythematous reaction or enhances this reaction in certain subjects, and can even be the source of phototoxic or photoallergic reactions. Thus, it is desirable to also screen out the UV-A radiation.

Many sunscreen compositions intended for photoprotection (UV-A and/or UV-B) of the skin are known to this art, and the use of inorganic nanopigments (namely, pigments, the average size of the primary particles of which does not generally exceed 100 nm) based on the metal oxides, and especially titanium dioxide, is becoming increasingly common in light of the fact that these, when they are combined with traditional UV screening agents (principally organic compounds capable of absorbing harmful radiation), provide a very high level of protection.

For a variety of reasons, associated especially with being more pleasant to use (gentleness, emollience, and the like), the sunscreen compositions currently available most typically are oil-in-water emulsions (namely, a vehicle comprising an aqueous continuous dispersing phase and an oily discontinuous dispersed phase) into which the aforesaid nanopigments have been introduced at various concentrations, where appropriate in combination with other, traditional UV screening agents. These may be present both in the aqueous phase of the emulsion and in its oily phase (also referred to as the "fatty" phase). In these traditional emulsions, which contain, in addition, emulsifying agents (or surfactants) and optionally common cosmetic additives such as perfumes, colorants, or preservatives, the size of the globules constituting the fatty phase is generally greater than several microns.

One of the major drawbacks of the known sunscreen compositions of the above type (O/W emulsion containing nanopigments), and more especially of those containing titanium dioxide $TiO_2$ nanopigments, is that, when applied to the skin in the form of a film, they whiten the skin which is cosmetically undesirable and generally disliked by the users. As the concentration of nanopigments in the emulsion is increased, this effect becomes more pronounced. To avoid this problem, it would naturally be possible to employ smaller amounts of the nanopigments but the resulting emulsions, which would admittedly produce films displaying acceptable transparency on the skin, would then no longer afford appropriate protection in the UV range, greatly limiting the value of same.

Moreover, another difficulty presented thereby is that the traditional sunscreen emulsions based on protective nanopigments provide, after topical application to the skin, an uneven, non-homogeneous or even crude distribution of the nanopigments on the skin, which can be detrimental to the quality of the desired global photoprotective response. This poor distribution of nanopigments on the surface of the skin is often the result of a substantial lack of homogeneity (poor dispersion of the pigment in its vehicle) in the initial emulsion itself (prior to application).

Lastly, with certain of the above-indicated sunscreen emulsions, and notwithstanding the fact that they contain emulsifying agents (or surfactants), a more or less lack of stability over time is observed, which is detrimental to their preservation once packaged (storage stability). This lack of stability manifests itself, in actual practice, in more or less marked phenomena of settling of the nanopigments within the emulsion, or even of separation between the aqueous and oily phases thereof.

SUMMARY OF THE INVENTION

Accordingly, a major object of the present invention is the provision of improved O/W type emulsions having sunscreen properties and comprising inorganic nanopigments based on metal oxides, which simultaneously display excellent transparency on the skin, very good efficacy of protection against UV irradiation, very good stability and perfect homogeneity both before and after topical application to the skin, i.e., the nanopigments are very well dispersed in the initial or beginning emulsion on the one hand, and on the skin after topical application on the other.

DETAILED DESCRIPTION OF BEST MODE AND PREFERRED EMBODIMENTS OF THE INVENTION

More particularly according to the present invention, it has now unexpectedly and surprising been found that the above-indicated disadvantages and drawbacks associated with the presence of photoprotective nanopigments in the traditional O/W emulsions of the prior art are avoided by employing specific "ultrafine" O/W emulsions, the size of the globules constituting the fatty phase of which being within well-defined limits. Such ultrafine O/W type emulsions are themselves preferably obtained via the so-called "phase inversion" technique more fully described below. All other factors being equal (i.e., with identical chemical compositions and concentrations), it is found that the sunscreen/cosmetic compositions according to the present invention, by simply adjusting the particle size of the oily globules to an appropriate value indicated below, consistently display, in particular in respect of their transparency on the skin, their stability, their homogeneity and their protective power, improved properties compared with the same sunscreen compositions not satisfying the aforesaid criterion of oil globule size.

Thus, the present invention features novel stable and homogeneous cosmetic, especially sunscreen compositions comprising, in a cosmetically acceptable vehicle, carrier or diluent of the oil-in-water emulsion type, inorganic nanopigments based on metal oxides as photoprotective agents, the average particle size of the globules which constitute the oily phase of said emulsion ranging from 100 nm to 1,000 nm.

The metal oxides suitable for formulation into the compositions of the present invention are per se known to this art for their photoprotective activity. Thus, these comprise, in particular, titanium, zinc, iron, zirconium and cerium oxides, or mixtures thereof.

Such nanopigments of metal oxides, whether coated or uncoated, are materials already well known to this art, and are, in particular, described in EP-A-0,518,773. Additional commercially available nanopigments, also suitable per the present invention, are those marketed under the trademarks UVT M 160, UVT M 212 and UVT M 262 by Kemira, and MT 100 SAS by Tayca.

In a preferred embodiment of the sunscreen compositions according to the invention, inorganic nanopigments based on titanium dioxide are used, which afford, in effect, the greatest efficacy in respect of photoprotection. Moreover, it should be appreciated that the undesirable cosmetic effect of whitening of the skin referred to above is especially pronounced with this type of nanopigment. This titanium dioxide can be in a crystalline form of the rutile and/or anatase type, and/or in an amorphous or substantially amorphous state. As indicated above, this pigment can then be coated or uncoated, but it is preferable to use pigments coated, for example, with alumina and/or aluminum stearate.

Depending on their more or less marked lipophilic or, to the contrary, hydrophilic nature or character, the nanopigments may be present either in the fatty phase of the emulsion, or in the aqueous phase, or even in both phases at the same time.

The average size of the primary particles of the nanopigments present in the compositions according to the invention generally ranges from 5 nm to 100 nm, and preferably from 10 to 50 nm.

Of course, the sunscreen compositions according to the invention can, in addition, contain one or more traditional hydrophilic or lipophilic organic sunscreen agents (absorbing agents) which are active in respect of UV-A and/or UV-B. Exemplary of such sunscreening agents are 2-phenylbenzimidazole-5-sulfonic acid and salts thereof, cinnamic derivatives such as, for example, 2-ethylhexyl-p-methoxycinnamate, salicylic derivatives such as, for example, 2-ethylhexyl salicylate and homomenthyl salicylate, camphor derivatives such as, for example, 3-(4-methylbenzylidene)camphor or (1,4-divinylbenzene)camphorsulfonic acid, triazine derivatives such as 2,4,6-tris[p-(2'-ethylhexyl-1'-oxycarbonyl)anilino]-1,3,5-triazine, benzophenone derivatives such as 2-hydroxy-4-methoxybenzophenone, dibenzoylmethane derivatives such as 4-tert-butyl-4'-methoxydibenzoylmethane, $\beta,\beta$-diphenylacrylate derivatives such as 2-ethylhexyl $\alpha$-cyano-$\beta,\beta$-diphenylacrylate, p-aminobenzoic acid derivatives such as, for example, octyl para-dimethylaminobenzoate, menthyl anthranilate and the screening polymers and screening silicones described in WO-93/04,665. Other examples of organic screening agents are presented in EP-A-0,487,404.

The nature of the fatty phase constituting the composition of the emulsions according to the invention is not critical, and can thus comprise all compounds which are generally known to this art as being suitable for the production of oil-in-water type emulsions. In particular, these compounds may be selected, whether singly or in admixture, from among the various fats, oils of vegetable, animal or mineral origin, natural or synthetic waxes, and the like.

Among the oils which can comprise the fatty phase, particularly exemplary thereof are:

(a) mineral oils such as paraffin oil and liquid petrolatum, (b) oils of animal origin such as perhydrosqualene, (c) oils of vegetable origin such as sweet almond oil, avocado oil, castor oil, olive oil, jojoba oil, sesame oil, groundnut oil, grape-pip oil, rapeseed oil, coconut oil, hazelnut oil, shea butter, palm oil, apricot-kernel oil, calophyllum oil, rice-bran oil, maize-germ oil, wheat-germ oil, soya-bean oil, sunflower oil, evening primrose oil, safflower oil, passion-flower oil and rye oil, (d) synthetic oils such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene gylcol dicaprylate and esters derived from lanolic acid such as isopropyl lanolate and isocetyl lanolate, isoparaffins and poly-$\alpha$-olefins.

Other oils suitable for use in the emulsions according to the invention include the benzoates of $C_{12}$–$C_{15}$ fatty alcohols (Finsolv TN marketed by FINETEX), fatty alcohols such as lauryl, cetyl, myristyl, stearyl, palmitryl and oleyl alcohol, as well as 2-octyldodecanol, acetylgylcerides, the octanoates and decanoates of alcohols and of polyols such as those of glycol and of glycerol, the ricinoleates of alcohols and of polyols such as cetyl ricinoleates, the trigylcerides of fatty acids such as caprylic/capric trigylcerides, triglycerides of $C_{10}$–$C_{18}$ saturated fatty acids, fluorinated and perfluorinated oils, lanolin, hydrogenated lanolin, acetylated lanolin and, lastly, silicone oils, whether volatile or otherwise.

It will of course be appreciated that the fatty phase can also contain one or more traditional lipophilic cosmetic adjuvants, in particular those which are typically incorporated into cosmetic sunscreen compositions.

According to an essential feature of the present invention, the average size of the liquid particles (or globules) of the fatty phase dispersed within the aqueous dispersing phase must satisfy very particular limits, namely, ranging from 100 nm to 1,000 nm. Preferably this average size ranges from 100 nm to 500 nm. Even more preferably, the size distribution of the oily globules is such that the size of most of said globules (i.e., at least 90% in numerical terms) is within the limits indicated above.

In conventional manner, the aqueous dispersing phase can comprise water, or a mixture of water and polyhydric alcohol(s) such as, for example, gylcerol, propylene gylcol and sorbitol, or, alternatively, a mixture of water and water-soluble lower alcohol(s) such as ethanol, isopropanol or butanol (aqueous-alcoholic solution), and it can naturally contain, in addition, traditional water-soluble cosmetic adjuvants.

Exemplary traditional cosmetic adjuvants suitable for the aqueous phase and/or the fatty phase of the emulsions according to the invention (depending on their water- and/or fat-soluble characteristics), are, in particular, ionic or nonionic thickeners, demulcents, antioxidants, opacifiers, stabilizers, emollients, insect repellents, hydrating agents, vitamins, perfumes, preservatives, fillers, sequestering agents, colorants, or any other constituent typically formulated into sunprotection products.

The emulsions according to the invention advantageously contain, in addition, particular surfactants or emulsifiers, the use of which is necessary for preparing and obtaining the ultrafine emulsion, as more fully described below. These can, in addition, contain specific coemulsifiers, the function of which is to decrease substantially, during the preparation of the emulsion, the amount of surfactants required for producing the emulsion.

For example, the sunscreen/cosmetic formulations according to the invention typically comprise the following compositions:

(i) aqueous phase: from 50% to 95% by weight, and preferably from 70% to 90% by weight, relative to the total formulation, (ii) oily phase: from 5% to 50% by weight, and preferably from 10% to 30% by weight, relative to the total formulation, (iii) nanopigments: from 0.5% to 40% by weight, and preferably from 1% to 30% by weight, relative to the total formulation, (iv) (co)emulsifier(s): from 0.5% to 20% by weight, and preferably from 2% to 10% by weight, relative to the total formulation.

A preferred process for formulating the compositions according to the invention, will now be more fully described.

As indicated above, this process is based on the technique of preparation of O/W emulsions by phase inversion. The principle of this technique is well known to this art, and is described, in particular, in the publication "Phase Inversion Emulsification" by T. Förster et al., appearing in *Cosmetics & Toiletries*, vol. 106, December 1991, pp. 49–52. Its principle is thus as follows: an emulsion is prepared (introduction of water into oil) at a temperature which must be above the phase inversion temperature (or PIT) of the system, namely, the temperature at which the balance between the hydrophilic and lipophilic properties of the emulsifier(s) employed is attained. At high temperature (>PIT), the emulsion is of the water-in-oil type and, as it cools, at the phase inversion temperature, this emulsion inverts to become an emulsion which is now of the oil-in-water type, having first transferred through a microemulsion state.

Per an essential feature of this invention, nanopigments must be present in the final ultrafine O/W emulsion. Thus, in a first embodiment of the preparative process according to the invention, the phase inversion of the emulsion is conducted in the presence of the photoprotective nanopigments described above; in a second embodiment of this process, these nanopigments are introduced only after the emulsion resulting from phase inversion has been obtained. It is of course possible to utilize both embodiments concurrently.

One of the difficulties in carrying out a process such as that indicated above center about appropriate selection of the emulsifying system which must be suited to the desired result.

The emulsifying systems which must thus be used are those which actually permit stable ultrafine emulsions resulting from phase inversion (100 nm$<\phi_{globules}<$1000 nm) to be obtained, and in which the nanopigments are dispersed finely and homogeneously.

It has thus been shown that, to this end, the emulsifying systems appropriate to the present invention are nonionic type emulsifiers, and, more particularly, are polyoxyethylenated and/or polyoxypropylenated fatty alcohols (i.e., compounds prepared by reacting an aliphatic fatty alcohol such as behenyl or cetyl alcohol with ethylene oxide or propylene oxide or an ethylene oxide/propylene oxide mixture) and fatty acid esters of polyols, optionally polyoxyethylenated and/or polyoxypropylenated (i.e., compounds prepared by reacting a fatty acid such as stearic acid or oleic acid with a polyol such as, for example, an alkylene glycol or glycerol or a polyglycerol, optionally in the presence of ethylene oxide or propylene oxide or an ethylene oxide/propylene oxide mixture), or mixtures thereof. Moreover, also preferably, the emulsifying system selected will possess an overall HLB (as is well known, HLB (hydrophilic-lipophilic balance in Griffin's sense; see *J. Soc. Cosm. Chem.*, vol. 5, pp. 249–256 (1954)), indicating the balance between the hydrophilic character and the lipophilic character of the surfactant) ranging from 9.5 to 11.5, approximately, and advantageously close to 10, such as to permit a phase inversion to be attained at a temperature below 90° C. (PIT <90° C.).

Unexpectedly and surprisingly, the presence of inorganic nanopigments in the initial system to be emulsified in no manner interferes with the mechanisms which are naturally involved in a phase inversion emulsification process. To the contrary, an ultrafine emulsion is produced in which the particles constituting the nanopigments are themselves maintained in a state of a fine dispersion (absence of agglomeration, or extremely small size of agglomerates) which is perfectly homogeneous and stable over time.

The preparative process according to the invention is described in the examples to follow.

The present invention also features the use of the compositions described above, as, or for the manufacture of, sunscreen/cosmetic compositions which protect the human epidermis or human hair against the deleterious effects of ultraviolet rays, or as sunscreen compositions, per se. The compositions may then be packaged in the form of creams, milks, cream gels or, alternatively, fluid lotions, especially vaporizable fluid lotions (the compositions according to the invention possessing, in effect, the additional advantageous property of being readily diluted in water).

The cosmetic treatment of the skin or hair according to this invention, intended to protect same against the deleterious effects of UV irradiation, especially that comprising solar radiation, entails applying to the skin or hair an effective amount of a cosmetic composition as described above.

In order to further illustrate the present invention and the advantages thereof, the following specific examples are given, it being understood that same are intended only as illustrative and in nowise limitative.

EXAMPLE 1

In this example, two formulations of the same chemical composition and containing $TiO_2$ nanopigments were prepared and compared, one being according to the invention (F1), ultrafine and obtained by phase inversion, the other being comparative (F2), non-ultrafine ($\phi_{globules} > 1$ μm) and obtained without employing phase inversion.

The procedure which was carried out for preparing these two compositions was as follows: the fatty (A) and aqueous (C) phases were both previously heated to a temperature on the order of 90° C. The phase (B) containing the nanopigments was then introduced and dispersed in the fatty phase (A), with vigorous stirring of the latter by means of a MORITZ type turbo-mixer (1,000 rpm). Lastly, the aqueous phase (A) was added to the resulting dispersion, still with mechanical stirring: in the case of the formulation (1), this final emulsification step was performed at 80° C., namely, at a temperature above the inversion temperature of the system, which in this instance was 72° C. (PIT), whereas in the case of the formulation (2), the emulsification was carried out at 55° C. (i.e., ToG<PIT).

The chemical compositions (% by weight relative to the total weight of the formulation) were as follows:

Phase A:

| | |
|---|---|
| (a) Cetyl/stearyl alcohol containing 15 EO, marketed under the trademark MERGITAL CS 15 by Henkel: | 6.6% |
| (b) Glyceryl stearate marketed under the trademark TEGIN 90 by Goldschmidt: | 3.4% |
| (c) Liquid petroleum: | 45.0% |

Phase B:

| | |
|---|---|
| (a) Nanopigmentary titanium dioxide $TiO_2$, marketed under the trademark MT 100T by Tayca: | 5% |

Phase C:

| | |
|---|---|
| (a) Glycerol: | 5% |
| (b) Preservatives: | qs % |
| (c) Water: | qs 100% |

For the formulations 1 and 2 thereby obtained, the following were then compared:

(i) the characteristics of the emulsions in respect of the size of the oil globules (optical microscope mag.×400);

(ii) the quality of dispersion of the pigment in the emulsion (optical microscope mag.×100);

(iii) their stability to heat on the one hand (45° C.), and to centrifugation on the other (30 min at 3,000 rpm).

The results obtained are reported in Table 1 below. These demonstrate clearly the superiority of the formulation according to the invention in respect of the quality of the dispersion of the pigment on the one hand, and the stability on the other.

Moreover, the two formulations F1 and F2 were evaluated in respect of their transparency on the skin of three control human subjects (P1, P2 and P3). These formulations were thus applied, on the basis of 2 mg/cm$^2$ of skin, to the forearms of the control population (squares of approximately 6 cm$^2$), and the colorimetric difference in the L, $a$, and $b$ values (trichromatic coordinates measured using a MINOLTA CM 1000 colorimeter) were measured on these forearms before and after application, such as to determine an absolute value ΔE which mirrors the overall modification of the skin coloration after application of the formulations:

$$\Delta E = (\Delta L^2 + \Delta a^2 + \Delta b^2)^{1/2}$$

The results obtained are reported in Table 1 below. These results show clearly that the mean change in coloration of the skin is less in the case of the application of the composition F1 according to the invention, reflecting a better transparency on the skin.

TABLE I

| | | | STABILITY | | ΔE | | | |
|---|---|---|---|---|---|---|---|---|
| | EMULSION FORM | PIGMENT DISPERSION | 45° C. | Centri-fugation | P1 | P2 | P3 | M[1] σ[2] |
| F1 | ULTRAFINE, no oily globules visible with an optical microscope ($\phi < 1$ μm) | (i) fine and homogeneous (ii) absence of agglomerates larger than 3 μm in size | stable after 10 days | stable | 2 | 3.5 | 2.7 | 2.7 0.7 |
| F2 | oily globules visible with an optical microscope ($\phi > 1$ μm) | (i) coarse (ii) many agglomerates larger than 10 μm in size | appearance of two phases and settling of the pigment after 48 hours | settling of the pigment | 3.3 | 5.7 | 5.3 | 4.8 1.3 |

[1]: mean
[2]: standard deviation

The totality of the above results demonstrate that the compositions according to the invention simultaneously present the three advantages comprising transparency on the skin, quality of dispersion of the pigment and stability.

EXAMPLES 2 to 6

Additional specific examples of compositions according to the invention are presented below:

| SUNSCREEN CREAM: | | | |
|---|---|---|---|
| (A) | (i) | Oxyethylenated cetyl/stearyl alcohol (12 EO) (Eumulgin B1 marketed by Sidobre Sinnova): | 3.3 g |
| | (ii) | Glyceryl monostearate (Tegin 90 marketed by Goldschmidt: | 1.7 g |
| | (iii) | Polydecene (Ethyl Flo 362 NF marketed by Ethyl Corporation): | 10 g |
| | (iv) | Dioctylcyclohexane (Cetiol S marketed by Sidobre Sinnova): | 6 g |
| | (v) | Cyclopentadimethylsiloxane (DC 245 Fluid marketed by Dow Corning): | 6 g |
| (B) | (i) | Aluminum stearate-treated $TiO_2$ (MT - 100T marketed by Tayca): | 5 g |
| (C) | (i) | Glycerol: | 3 g |
| | (ii) | Water: | 15 g |
| (D) | (i) | Hydroxyethylcellulose (Natrosol 250HHR marketed by Aqualon): | 0.6 g |
| | (ii) | Water: | qs 100 g |
| (E) | (i) | Preservative: | qs |
| (F) | (i) | Perfume: | qs |

Method of Preparation
(1) Prepare the gel D with stirring at 60° C.;
(2) Heat the phases A and C at 90° C.;
(3) Disperse the pigment B in the phase A, then add the phase C with Moritz apparatus stirring (1,500 rpm);
(4) At about 40° C., add the gel D, then E and F.

| SUNSCREEN MILK: | | | |
|---|---|---|---|
| (A) | (i) | Oxyethylenated cetyl/stearyl alcohol (15 EO) (Mergital CS 15 marketed by Henkel): | 4.4 g |
| | (ii) | Glyceryl monostearate (Tegin 90 marketed by Goldschmidt: | 2.3 g |
| | (iii) | Liquid petrolatum: | 20 g |
| | (iv) | 2-Ethylhexyl p-methoxycinnamate (Parsol MCX marketed by Givaudan): | 3 g |
| | (v) | Di-n-octyl ether (Cetiol OE marketed by Sidobre Sinnova): | 7 g |
| (B) | (i) | $TiO_2$ treated with $SiO_2/Al_2O_3$ and polydimethylsiloxane (UVT - M262 marketed by Kemira): | 2 g |
| (C) | (i) | Glycerol: | 5 g |
| | (ii) | Water: | 15 g |
| (D) | (i) | Hydroxyethylcellulose (Natrosol-250HHR marketed by Aqualon): | 0.3 g |
| | (ii) | Water: | qs 100 g |
| (E) | (i) | Preservative: | qs |
| (F) | (i) | Perfume: | qs |

Method of Preparation
(1) Prepare the gel D with stirring at 60° C.;
(2) Heat the phases A and C at 90° C.;
(3) Disperse the pigment B in the phase A, then add the phase C with Moritz apparatus stirring (1,500 rpm);
(4) At about 40° C., add the gel D, then E and F.

| SUNSCREEN LOTION: | | | |
|---|---|---|---|
| (A) | (i) | Oxyethylenated behenyl alcohol (10 EO) (Mergital B10 marketed by Sidobre Sinnova): | 5 g |
| | (ii) | Oxyethylenated lauryl alcohol (40 EO) (Brij 30 marketed by ICI): | 5 g |
| | (iii) | Polydecene (Ethyl Flo 362 NF marketed by Ethyl Corporation): | 10 g |
| | (iv) | Liquid petrolatum: | 10 g |
| (B) | (i) | Glycerol: | 5 g |
| | (ii) | Water: | 15 g |
| (C) | (i) | $SiO_2/Al_2O_3$-treated $TiO_2$ in 40% aqueous dispersion (Troveil AQ marketed by Trioxide): | 7.5 g |
| | (ii) | (1,4-Divinylbenzene)camphorsulfonic acid in 33% aqueous solution (Mexoryl SX marketed by Chimex): | 3.03 g |
| | (iii) | Triethanolamine: | 0.6 g |
| | (iv) | Water: | qs 100 g |
| (D) | (i) | Preservative: | qs |
| (F) | (i) | Perfume: | qs |

Method of Preparation
(1) Heat the phases A and C at 90° C.;
(2) Add B to A with Moritz apparatus stirring (1,500 rpm);
(3) At room temperature, with less vigorous stirring, add the phase C, then D and E.

| SUNSCREEN CREAM: | | | |
|---|---|---|---|
| (A) | (i) | Oxyethylenated cetyl/stearyl alcohol (12 EO) (Eumulgin B1 marketed by Sidobre Sinnova): | 3.6 g |
| | (ii) | Glyceryl monostearate (Tegin 90 marketed by Goldschmidt): | 1.4 g |
| | (iii) | 4-tert-Butyl-4'-methoxydibenzoylmethane (Parsol 1789 marketed by Givauden): | 1 g |
| | (iv) | Benzoate of $C_{12}/C_{15}$ alcohols (Finsolv TN marketed by Finetex): | 3 g |
| | (v) | 2-Ethylhexyl 2-cyano-3,3-di-phenylacrylate (Uvinul N539 marketed by BASF): | 2 g |
| | (vi) | Liquid petrolatum: | 15 g |
| (B) | (i) | Glycerol: | 5 g |
| | (ii) | Water: | 15 g |
| (C) | (i) | $SiO_2/Al_2O_3$-treated $TiO_2$ in 40% aqueous dispersion (Troveil AQ marketed by Trioxide): | 12.5 g |
| (D) | (i) | Crosslinked polyacrylic acid (Carbopol 980 marketed by Goodrich): | 0.21 g |
| | (ii) | Triethanolamine: | 0.26 g |
| | (iii) | Water: | qs 100 g |
| (E) | (i) | Preservative: | qs |
| (F) | (i) | Perfume | qs |

Method of Preparation
(1) Prepare the gel D with stirring at 60° C.;
(2) Heat the phases A and B to 90° C., add B to A with Moritz apparatus stirring (1,500 rpm);
(3) Disperse the pigment C in (A+B), then add the gel D at about 40° C., then E and F.

| SUNSCREEN MILK: | | | |
|---|---|---|---|
| (A) | (i) | Oxyethylenated glyceryl monostearate (20 EO) (Cutina E24 marketed by Sidobre Sinnova): | 3.3 g |
| | (ii) | Glyceryl monostearate (Tegin 90 marketed by Goldschmidt): | 1.7 g |
| | (iii) | Liquid petrolatum: | 15 g |
| | (iv) | Diisopropyl adipate: | 5 g |

SUNSCREEN MILK:

|     |       |                                                                                                                   |          |
| --- | ----- | ----------------------------------------------------------------------------------------------------------------- | -------- |
|     | (v)   | 2,4,6-Tris[p-(2'-ethylhexyl-1'-oxycarbonyl)anilino]-1,3,5-triazine (Uvinul-T150 marketed by BASF):                | 1 g      |
| (B) | (i)   | Aluminum stearate-treated $TiO_2$ (MT - 100T marketed by Tayca):                                                  | 3 g      |
| (C) | (i)   | Glycerol:                                                                                                         | 3 g      |
|     | (ii)  | Water:                                                                                                            | 15 g     |
| (D) | (i)   | Hydroxyethylcellulose (Natrosol 250HHR marketed by Aqualon):                                                      | 0.6 g    |
|     | (ii)  | Water:                                                                                                            | qs 100 g |
| (E) | (i)   | Preservative:                                                                                                     | qs       |
| (F) | (i)   | Perfume:                                                                                                          | qs       |

Method of Preparation (1) Prepare the gel D with stirring at 60° C.;

(2) Heat the phases A and C at 90° C.;

(3) Disperse the pigment B in the phase A, then add the phase C with Moritz apparatus stirring (1,500 rpm);

(4) At about 40° C., add the gel D, then E and F.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising a storage-stable, ultrafine oil-in-water emulsion of a photoprotecting effective amount of homogeneously and finely dispersed particulates of at least one inorganic nanopigment which comprises a metal oxide.

2. The sunscreen/cosmetic composition as defined by claim 1, the average particle size of the globules comprising the oily phase of said emulsion ranging from 100 nm to 1,000 nm.

3. The sunscreen/cosmetic composition as defined by claim 2, the average particle size of the globules comprising the oily phase of said emulsion ranging from 100 nm to 500 nm.

4. The sunscreen/cosmetic composition as defined by claim 2, at least 90% of said globules having a particle size ranging from 100 nm to 1,000 nm.

5. The sunscreen/cosmetic composition as defined by claim 3, at least 90% of said globules having a particle size ranging from 100 nm to 500 nm.

6. The sunscreen/cosmetic composition as defined by claim 2, the average size of the primary particles comprising said nanopigment particulates ranging from 5 nm to 100 nm.

7. The sunscreen/cosmetic composition as defined by claim 6, the average size of the primary particles comprising said nanopigment particulates ranging from 10 nm to 50 nm.

8. The sunscreen/cosmetic composition as defined by claim 2, said at least one inorganic nanopigment comprising an oxide of titanium, zinc, iron, zirconium, or cerium, or mixture thereof.

9. The sunscreen/cosmetic composition as defined by claim 8, said at least one inorganic nanopigment comprising titanium dioxide.

10. The sunscreen/cosmetic composition as defined by claim 9, said at least one inorganic nanopigment comprising particulates of titanium dioxide coated with alumina and/or aluminum stearate.

11. The sunscreen/cosmetic composition as defined by claim 9, said at least one inorganic nanopigment comprising a crystalline titanium dioxide.

12. The sunscreen/cosmetic composition as defined by claim 11, said at least one inorganic nanopigment comprising an amorphous titanium dioxide.

13. The sunscreen/cosmetic composition as defined by claim 2, further comprising at least one organic UV-A and/or UV-B sunscreen.

14. The sunscreen/cosmetic composition as defined by claim 2, the oily phase of said emulsion comprising a cosmetically acceptable fat, oil, wax, or mixture thereof.

15. The sunscreen/cosmetic composition as defined by claim 2, further comprising at least one emulsifying agent.

16. The sunscreen/cosmetic composition as defined by claim 15, comprising from 0.5% to 40% by weight thereof of said at least one emulsifying agent.

17. The sunscreen/cosmetic composition as defined by claim 16, comprising from 2% to 10% by weight thereof of said at least one emulsifying agent.

18. The sunscreen/cosmetic composition as defined by claim 2, the aqueous phase of said emulsion comprising water, admixture of water and at least one polyhydric alcohol, or admixture of water and at least one water-soluble lower alcohol.

19. The sunscreen/cosmetic composition as defined by claim 2, further comprising at least one cosmetically acceptable adjuvant or additive.

20. The sunscreen/cosmetic composition as defined by claim 19, said at least one adjuvant or additive comprising an ionic or nonionic thickener, demulcent, antioxidant, opacifier, stabilizer, emollient, insect repellent, hydrating agent, filler, vitamin, perfume, preservative, sequestering agent, colorant, or mixture thereof.

21. The sunscreen/cosmetic composition as defined by claim 2, the aqueous phase of said emulsion comprising from 50% to 95% by weight thereof.

22. The sunscreen/cosmetic composition as defined by claim 21, the aqueous phase of said emulsion comprising from 70% to 90% by weight thereof.

23. The sunscreen/cosmetic composition as defined by claim 21, the oily phase of said emulsion comprising from 5% to 50% by weight thereof.

24. The sunscreen/cosmetic composition as defined by claim 22, the oily phase of said emulsion comprising from 10% to 30% by weight thereof.

25. The sunscreen/cosmetic composition as defined by claim 23, the nanopigment particulates comprising from 0.5% to 40% by weight thereof.

26. The sunscreen/cosmetic composition as defined by claim 25, said nanopigment particulates comprising from 1% to 30% by weight thereof.

27. The sunscreen/cosmetic composition prepared by a process comprising the following steps (i) emulsifying the aqueous phase into the oil phase thereof, at a temperature above the phase inversion temperature of the medium, (ii) cooling the water-in-oil emulsion thus obtained to a temperature below said phase inversion temperature, thereby converting said water-in-oil emulsion into said ultrafine oil-in-water emulsion, and (iii) introducing said nanopigment particulates into the medium of emulsion either during the step (i) and/or after the step (ii).

28. The sunscreen/cosmetic composition as defined by claim 1, comprising a cream, gel, milk or lotion.

29. A sunscreen/cosmetic composition produced according to claim 27.

30. A sunscreen/cosmetic composition according to claim 27, said at least one nonionic surfactant comprising a polyoxyetylenated and/or polyoxypropylenated fatty alcohol, an optionally polyoxyethylenated and/or polyoxypropylenated fatty acid ester of a polyol, or mixture thereof.

31. A sunscreen/cosmetic composition according to claim 27, where in step (i) the medium of emulsion has an overall HLB ranging from 9.5 to 11.5.

32. A sunscreen/cosmetic composition according to claim 30, said overall HLB being approximately 10.

33. The sunscreen/cosmetic composition of claim 27, the average possible size of the globules comprising the oily phase of said emulsion ranging from 100 nm to 1000 nm.

34. The sunscreen/cosmetic composition of claim 33, the average particle size of the globules comprising the oily phase of said emulsion ranging from 100 nm to 500 nm.

* * * * *